United States Patent
Mehta

(10) Patent No.: US 6,756,410 B2
(45) Date of Patent: Jun. 29, 2004

(54) INDUCTION OF LDL RECEPTOR EXPRESSION BY EXTRACELLULAR-SIGNAL REGULATED KINASE, ERK-1/2

(76) Inventor: Kamal D. Mehta, 13212 Fairway Village Ct., Little Rock, AR (US) 72212

( * ) Notice: Subject to any disclaimer, the term of this patent is extended or adjusted under 35 U.S.C. 154(b) by 21 days.

(21) Appl. No.: 09/942,320

(22) Filed: Aug. 29, 2001

(65) Prior Publication Data

US 2002/0082192 A1 Jun. 27, 2002

Related U.S. Application Data

(60) Provisional application No. 60/229,271, filed on Aug. 30, 2000.

(51) Int. Cl.[7] .......................... A01N 25/00; C12Q 1/48; C12Q 1/68
(52) U.S. Cl. ................ 514/789; 435/15; 435/6
(58) Field of Search ............ 514/789; 435/15, 435/6, 194

(56) References Cited

PUBLICATIONS

Kumar et al., J. Lipid Research, 38, 2240–2248, 1997.*
Dhawan et al., J. Lipid Research, 40, 1911–1919, 1999.*
Dhawan et al., FASEB. J., Mar. 12, 1999, vol. 13(4), part 1, pp. A194.*

* cited by examiner

Primary Examiner—Maryam Monshipouri
(74) Attorney, Agent, or Firm—Benjamin Aaron Adler

(57) ABSTRACT

Specific activation of the Raf-1/MEK/p42/44$^{MAPK}$ kinase cascade in HepG2 cells, independent of other "upstream" factors or cell growth regulation, leads to induction of LDL receptor transcription. The degree of p42/44$^{MAPK}$ activation determines the extent of LDL receptor induction. The present findings underscore the important and central role of the MAPK pathway in regulating low density lipoprotein receptor expression and may be of considerable potential significance for the development of new signal transduction-based approaches for the treatment of hypercholesterolemia.

3 Claims, 14 Drawing Sheets

INDUCTION OF LDL RECEPTOR EXPRESSION BY EXTRACELLULAR-SIGNAL REGULATED KINASE, ERK-1/2

CROSS-REFERENCE TO RELATED APPLICATION

This non-provisional patent application claims benefit of U.S. Ser. No. 60/229,271, filed Aug. 30, 2000, now abandoned.

FEDERAL FUNDING LEGEND

This invention was produced in part using funds obtained through a grant from the National Institutes of Health. Consequently, the federal government has certain rights in this invention.

BACKGROUND OF THE INVENTION

1. Field of the Invention

The present invention relates generally to the fields of biochemistry and molecular biology. More specifically, the present invention relates to the role of p42/44$^{MAPK}$ (also known as extracellular-signal regulated kinase, ERK-1/2) in the induction of low density lipoprotein (LDL) receptor expression.

2. Description of the Related Art

Mitogen-activated protein kinases (MAPK) are cellular signaling pathways that enable cells to transduce extracellular signals into an intracellular response (Robinson and Cobb, 1997; Schaeffer and Weber, 1999). In mammalian cells, three parallel MAPK pathways have been identified. The classical p42/44$^{MAPK}$ pathway is activated in response to signals from cell surface receptors, followed by activation of Raf-1 kinase and MAPK kinase (MEK), which directly activates p42/44$^{MAPK}$ (also known as extracellular-signal regulated kinase, ERK-1/2) through phosphorylation at regulatory threonine and tyrosine residues. In contrast, p38$^{MAPK}$ and p46/54$^{JNK}$ pathways are primarily activated by cellular stress signals such as proinflammatory cytokines, heat shock, or UV light and have therefore also been described as "stress-activated protein kinases" (Whitmarsh and Davis, 1996; Garrington and Johnson, 1999). The signals transmitted through the p42/44$^{MAPK}$ cascade lead to activation of a set of regulatory molecules that play a key role in a variety of cellular responses, including proliferation, differentiation, and cell death. From the published reports, it is evident that the magnitude and duration of p42/44$^{MAPK}$ activation appears to be a key determinant in cell fate signaling (Marshal, 1995; Pumiglia and Decker, 1997; Bornfeldt et al., 1997).

It is now well accepted that relationships exist among the processes of cell growth and those of cholesterol synthesis and metabolism (Habenicht et al., 1984; Fairbank et al., 1984; Casey et al., 1989; Hancock et al., 1989; Gutrierrez et al., 1989; Goldstein and Brown, 1990). Mammalian cells require cholesterol as a structural component of their plasma membrane and other membranes. Cholesterol required for membrane biosynthesis can be derived either from endogenous synthesis within the cell or from an exogenous source. Under normal conditions, many cell types primarily obtain cholesterol from exogenous low density lipoprotein (LDL) via the low density lipoprotein receptor pathway (Brown and Goldstein, 1986).

To investigate the role of the p42/44$^{MAPK}$ signaling cascade in regulating LDL receptor expression, a specific, cell-permeable, noncompetitive inhibitor of MEK-1/2, PD98059 ([2-(2'-amino-3'-methoxyphenyl)-oxanaphthalene-4-one]) (Pang et al., 1995), was utilized. A requirement of the p42/44$^{MAPK}$ cascade during induction of LDL receptor expression in response to a variety of agents, including phorbol-esters, hepatocyte growth factor, interleukin-1β, and anisomycin (Kumar et al., 1997; Kumar et al., 1998; Singh et al., 1999; Dhawan et al., 1999; Mehta and Miller, 1999). Investigations by other laboratories also supported the requirement of the p42/44$^{MAPK}$ signaling cascade in insulin and oncostatin-induced LDL receptor expression (Kotzka et al., 2000; Liu et al., 2000). Taken together, these studies showed that different extracellular signals require signaling through p42/44$^{MAPK}$ to induce LDL receptor expression.

However, given the complexities of cytokine/growth factor signaling, a number of questions were raised by these initial and limited studies, including the following: (i) What is the relationship between p42/44$^{MAPK}$ activation, low density lipoprotein receptor expression and cell growth? (ii) Is activation of p42/44$^{MAPK}$ alone sufficient to induce low density lipoprotein receptor expression, or is participation of other signaling pathways along with p42/44$^{MAPK}$ required for induction of low density lipoprotein receptor expression? (iii) What is the nature of p42/44$^{MAPK}$-mediated low density lipoprotein receptor induction in terms of sterol sensitivity?

Thus, the prior art is deficient in identifying a direct role of p42/44$^{MAPK}$ in the induction of LDL receptor expression. The present invention fulfills this long-standing need and desire in the art.

SUMMARY OF THE INVENTION

The present study reports the results of studies designed to address the relationship between p42/44$^{MAPK}$ activation and IDL receptor expression. A HepG2-derived cell line that stably expresses an inducible form of Raf-1:ER, a fusion protein consisting of an oncogenic form of human Raf-1 kinase (amino acids 305 to 648 that encode all of the kinase domain contained in conserved region 3 but none of conserved regions 1 or 2) and the hormone-binding domain of the human estrogen receptor was generated. It was shown that specific activation of the Raf-11/MEK/p42/44$^{MAPK}$ cascade by ICI182,780 induces low density lipoprotein receptor expression and modulation of the Raf-1 kinase signal strength is sufficient to determine low density lipoprotein receptor expression levels. Interestingly, Raf-1 kinase activation inhibited DNA synthesis and caused growth arrest, indicating that activation of the Raf-1/MEK/p42/44$^{MAPK}$ cascade uncouples regulation of low density lipoprotein receptor expression from cell growth and these two processes can be regulated independently.

The findings reported here may be of considerable potential significance with regard to the process of low density lipoprotein receptor regulation in vivo. The present findings also underscore the important and central role of the MAPK pathway in regulating LDL receptor expression and may be of considerable potential significance for the development of new signal transduction-based approaches for the treatment of hypercholesterolemia.

In one embodiment of the present invention, there is provided a method of inducing LDL receptor expression through the sole activation of extracellular-signal regulated kinase (p42/44$^{MAPK}$) by contacting a cell with a compound that activates the extracellular-signal regulated kinase, p42/44$^{MAPK}$, wherein the activation of said kinase results in the induction of low density lipoprotein receptor expression. Generally, the induction of low density lipoprotein receptor expression is independent of cell growth regulation, whereas the extent of the induction of low density lipoprotein receptor expression is dependent on the extent of activation of p42/44$^{MAPK}$. Preferably, the cell is the HepG2-ΔRaf1:ER cell line.

In another embodiment of the present invention, there is provided a method of screening a candidate compound that induces p42/44$^{MAPK}$-mediated LDL receptor expression by contacting a cell that activates p42/44$^{MAPK}$ in response to extracellular stimulant with a candidate compound, followed by measuring the activation of p42/44$^{MAPK}$ and low density lipoprotein receptor expression. Activation of p42/44$^{MAPK}$ and induction of low density lipoprotein receptor expression in the presence of the compound is indicative of the compound's ability in inducing p42/44$^{MAPK}$-mediated low density lipoprotein receptor expression. Preferably, the cell is the HepG2-ΔRaf-1:ER cell line.

In still another embodiment of the present invention, there is provided a method of determining the level of low density lipoprotein receptor expression in an individual. This method comprises examining the level of p42/44$^{MAPK}$ expression in said individual. In general, high p42/44$^{MAPK}$ expression is indicative of high low density lipoprotein receptor expression, whereas low p42/44$^{MAPK}$ expression is indicative of low LDL receptor expression in said individual.

Other and further aspects, features, and advantages of the present invention will be apparent from the following description of the presently preferred embodiments of the invention. These embodiments are given for the purpose of disclosure.

BRIEF DESCRIPTION OF THE DRAWINGS

So that the matter in which the above-recited features, advantages and objects of the invention, as well as others which will become clear, are attained and can be understood in detail, more particular descriptions of the invention briefly summarized above may be had by reference to certain embodiments thereof which are illustrated in the appended drawings. These drawings form a part of the specification. It is to be noted, however, that the appended drawings illustrate preferred embodiments of the invention and therefore are not to be considered limiting in their scope.

FIG. 2 shows ICI182,780 treatment of HepG2-ΔRaf-1:ER cells induce p42/44$^{MAPK}$ phosphorylation and LDL receptor expression in a dose-dependent manner.

FIG. 3 shows pretreatment with staurosporine, or PD98059 abolished ICI182,780-induced p42/44$^{MAPK}$ phosphorylation and induction of LDL receptor expression.

FIG. 4 shows ICI182,780 treatments of HepG2-ΔRaf1:ER cells activate p42/44$^{MAPK}$ phosphorylation and induce LDL receptor expression in a time-dependent manner.

FIG. 5 shows sterols suppresses ICI182,780-dependent increase in LDL receptor expression without affecting p42/44$^{MAPK}$ activation.

FIG. 7 shows pretreatment of HepG2-ΔRaf-1:ER cells with curcumin blocked ICI182,780-induced LDL receptor expression without affecting p42/44$^{MAPK}$ phosphorylation.

FIG. 8 shows Raf-1/MEK-1/2/p42/44$^{MAPK}$ cascade activation causes cell growth arrest and inhibits DNA synthesis in HepG2-ΔRaf-1:ER cells.

DETAILED DESCRIPTION OF THE INVENTION

Figure 1:
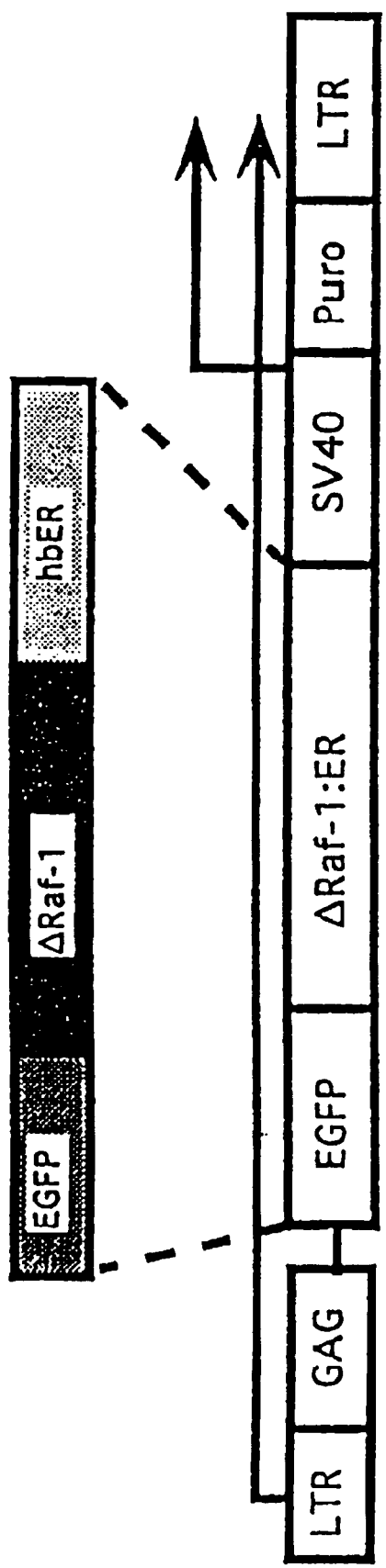
FIG. 1 shows schematic representation of a ΔRaf-1:ER construct used in this study. This construct encodes chimeric proteins consisting of green fluorescent protein (GFP) at the amino terminus, the [DD] form of the catalytic domain of Raf-1 in the middle, and the hormone binding domain of the human estrogen receptor (ER) at the carboxy terminus. As indicated, the expression of the ΔRaf-1:ER gene is promoted by the Moloney leukemia virus long-terminal repeat and expression of the puromycin-resistance gene is promoted by the SV40 early promoter.

Previous observations that induction of low density lipoprotein (LDL) receptor expression by a variety of extracellular signals is blocked by PD98059, a specific mitogen-activated protein kinase inhibitor, led to the suggestion that p42/44$^{MAPK}$ is critical in regulating LDL receptor expression. To analyze the specific contribution of the p42/44$^{MAPK}$ cascade during LDL receptor induction, a HepG2-derived cell line that stably expresses an inducible form of oncogenic human Raf-1 kinase activated by anti-estradiol ICI182,780 was established.

Using this system, direct evidence was provided that specific activation of this cascade alone is not only required but is sufficient to fully induce LDL receptor expression. The degree of p42/44$^{MAPK}$ activation determines the extent of LDL receptor induction. Inhibition of phosphorylation of Raf-1 and p42/44$^{MAPK}$ by staurosporine and PD98059, respectively, completely blocked LDL receptor induction by ICI182,780. Interestingly, ICI182,780-induced low density lipoprotein receptor expression was suppressed by sterols without affecting p42/44$^{MAPK}$ activation. Finally, addition of ICI182,780 to the modified cells led to inhibition of DNA synthesis, growth arrest, decrease in cyclin A and upregulation of p21$^{Cip}$ expression in a time-dependent manner, showing that p42/44$^{MAPK}$-induced low density lipoprotein receptor expression is independent of cell growth. Thus, Raf-1/MEK/p42/44$^{MAPK}$ plays a central role in regulating LDL receptor expression, and the extent of p42/44$^{MAPK}$ activation may be important in transducing divergent cellular responses with implications for altered signaling resulting in hypercholesterolemia.

In the present invention, there is provided a method of inducing LDL receptor expression through the sole activation of extracellular-signal regulated kinase (p42/44$^{MAPK}$) by contacting a cell with a compound that activates the extracellular-signal regulated kinase, p42/44$^{MAPK}$, wherein the activation of said kinase results in the induction of low density lipoprotein receptor expression. Generally, the induction of low density lipoprotein receptor expression is independent of cell growth regulation, whereas the extent of the induction of LDL receptor expression is dependent on the extent of activation of p42/44$^{MAPK}$. Preferably, the cell is the HepG2-ΔRaf-1:ER cell line.

The present invention is also directed to a method of screening candidate compounds that induce p42/44$^{MAPK}$-mediated LDL receptor expression. This method comprises contacting a cell that activates p42/44$^{MAPK}$ in response to extracellular stimulant with a candidate compound, followed by measuring the activation of p42/44$^{MAPK}$ and low density lipoprotein receptor expression. Activation of p42/44$^{MAPK}$ and induction of low density lipoprotein receptor expression in the presence of the compound is indicative of the compound's ability in inducing p42/44$^{MAPK}$-mediated LDL receptor expression. Preferably, the cell is the HepG2-ΔRaf-1:ER cell line.

Furthermore, since the p42/44$^{MAPK}$ pathway solely controls LDL receptor expression, individuals might differ in p42/44$^{MAPK}$ levels and therefore in their LDL receptor levels. Measurement of p42/44$^{MAPK}$ and/or downstream signaling cascade can then be used to explain differential responses within human population to high cholesterol diets. Thus, in the present invention, there is provided a method of determining the level of low density lipoprotein receptor expression in an individual by examining the level of p42/44$^{MAPK}$ expression in said individual. In general, high p42/44$^{MAPK}$ expression is indicative of high low density lipoprotein receptor expression, whereas low p42/44$^{MAPK}$ expression is indicative of low low density lipoprotein receptor expression in said individual.

The following examples are given for the purpose of illustrating various embodiments of the invention and are not meant to limit the present invention in any fashion.

EXAMPLE 1
Reagents and Antibodies

ICI182,780 was purchased from Tocris. PD98059, staurosporine, and curcumin were obtained from Calbiochem. 25-hydroxycholesterol and cholesterol were purchased from Sigma Chemical Compant and Steraloids, Inc., respectively. Puromycin was purchased from Sigma. Antibodies to phosphorylation independent and phospho-specific Raf-1 kinase (Ser259) were purchased from New England Biolabs. Phospho-specific antibodies to the activated forms of p42/44$^{MAPK}$ (Thr 202/Tyr 204) were also purchased from New England Biolabs. Antibodies to phosphorylation-independent p42/44$^{MAPK}$, cyclin A, and p21$^{Cip}$ were purchased from Santa Cruz Biotechnology. TRIzol and all tissue culture supplies were from Life Technologies, Inc. Zeta probe blotting membrane and the protein assay reagents were purchased from Bio-Rad. [α-$^{32}$P]dCTP (3000Ci/mmol) was obtained from DuPont, and the enhanced chemiluminescence (ECL) detection kit was obtained from Amersham Pharmacia Biotech. Plasmid encoding ΔRaf-1:ER was obtained from Dr. Martin McMahon, University of California, San Francisco (Woods et al., 1997). A light chemiluminescent reporter gene assay system for the detection of luciferase activity was purchased from TROPIX, Inc.

EXAMPLE 2
Cell Culture

Human hepatoma HepG2 cell line and its derivative HepG2-ΔRaf-1:ER cell line that stably expresses the ΔRaf-1:ER chimera were maintained as monolayer cultures in a humidified 5% $CO_2$ atmosphere at 37° C. in Eagle's minimum essential medium (BioWhitaker) supplemented with 10% fetal bovine serum (Life Technologies), 2 mM L-glutamine, 20 units/ml penicillin, and 20 μg/ml streptomycin sulfate. In addition, puromycin (2 μg/ml) was added to maintain selection pressure for HepG2-ΔRaf-1:ER cells.

EXAMPLE 3
Northern Blot Analysis

Total RNA was isolated by the TRIzol reagent (GIBCO-BRL), according to the manufacturer's protocol. RNA was stored under ethanol. Aliquots containing 20 μg RNA were electrophoresed through a 1%-agarose-formaldehyde gel and transferred to a nylon membrane (BioRad) followed by hybridization. Hybridization probes for LDL receptor, actin, and SS, labeled with $^{32}$P, were prepared using the M13 universal primer. Hybridizations were performed at 45° C., and after final washing at 55° C. for 30 min, filters were exposed to Kodak x-ray film. The relative intensities of specific bands were determined densitometrically within the linear range of film on a model 300A laser densitometer (Molecular Dyanamics) using Image Quant software.

EXAMPLE 4
Preparation of Cell Extracts and Immunoblot Analysis

Cells were scraped in phosphate-buffered saline (PBS) and centrifuged, and the pellet was resuspended in lysis buffer (50 mM Tris-Cl [pH 7.5], 150 mM NaCl, 10 mM $MgCl_2$, 1 mM dithiothreitol, 10 mM NaF, 0.5 mM $Na_3VO_4$, 0.5% Nonidet P-40, 10 μg of aprotinin/ml, and 100 μg of phenylmethylsulfonyl fluoride per ml). Protein concentration was measured by the Bio-Rad protein assay. Protein (30 to 50 μg) was resolved by sodium dodecyl sulfate-polyacrylamide gel electrophoresis (SDS-PAGE) and transferred onto Immobilon P membranes (Millipore). The filter was blocked in 2.5% skim milk with 0.1% Tween 20 in PBS for 2 h followed by incubation with the specific antibody. The following antibodies were used: polyclonal rabbit antibodies against phosphorylation-independent p42/44$^{MAPK}$, phospho-specific-p42/44$^{MAPK}$, and phospho-specific or phosphorylation-independent Raf-1 kinase. Reactive proteins were detected with horseradish peroxidase-conjugated secondary antibodies and visualized with an ebb enhanced chemiluminescence detection kit (Amersham Pharmacia Biotech).

EXAMPLE 5
Transfection and Luciferase Assays

Figure 6:
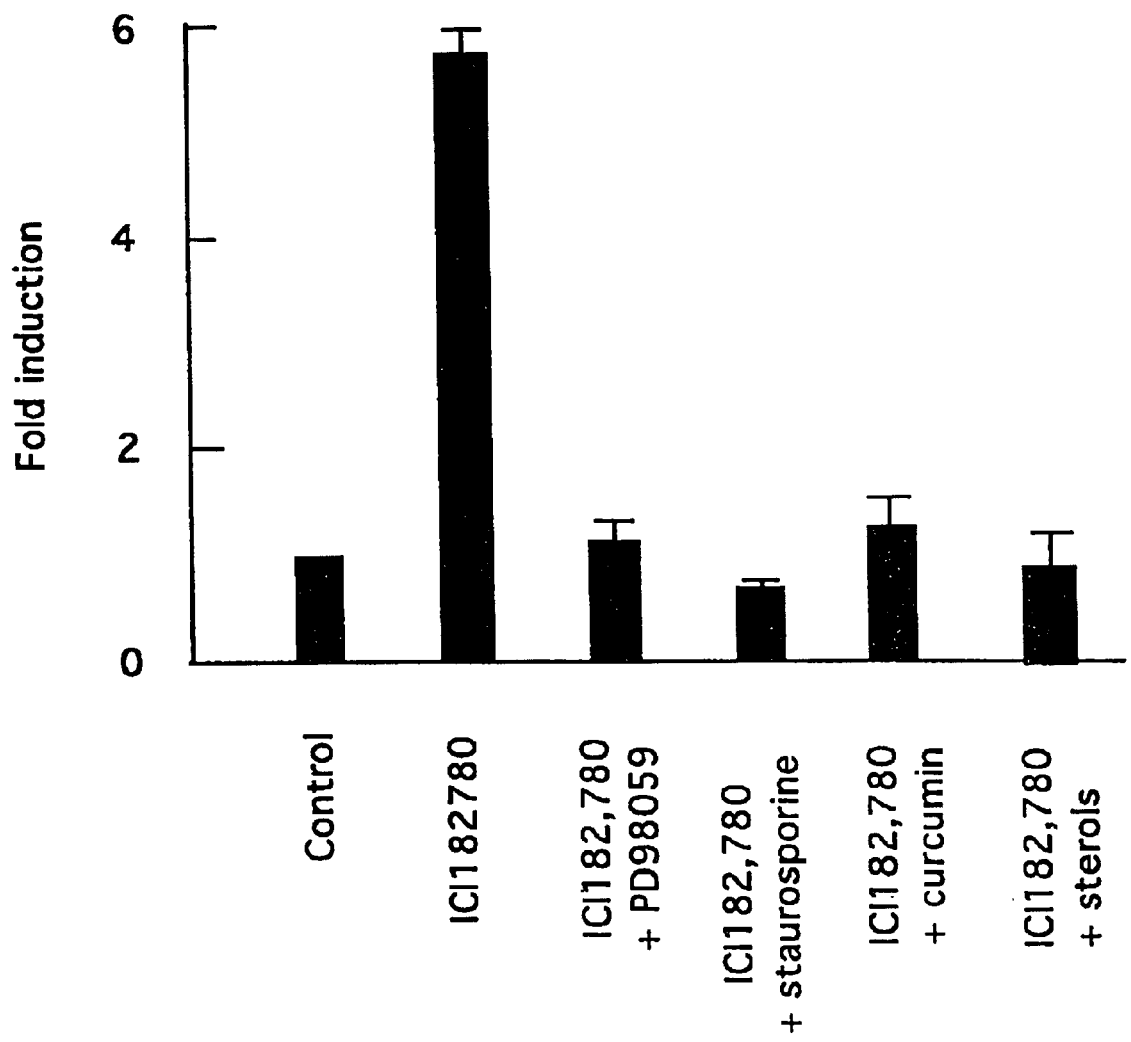
FIG. 6 shows that ICI182,780 induces LDL receptor gene expression at the transcriptional level. HepG2-ΔRaf-1:ER cells were cotransfected with LDL receptor promoter-luciferase reporter (plasmid A) and β-galactosidase-reporter. After 24 hours, cells were grown in a medium containing 0.2% serum for 12 h, followed by addition of 1 μM ICI182,780 for the last 24 h in the absence or presence of indicated inhibitor. The concentrations used for PD98059, staurosporine, and curcumin were 50 μM, 1 μM, and 20 μM, respectively. Sterols (2 μg/ml 25-hydroxycholesterol and 10 μg/ml cholesterol) were added to examine sensitivity to sterols. After the treatment both luciferase and β-galactosidase activities were measured according to the method previously described (24). The results are presented as means ±S.E. and represent at least three individual experiments.

A human low density lipoprotein receptor promoter-luciferase construct A (24) was used to determine the response of the low density lipoprotein receptor promoter to activation of the p42/44$^{MAPK}$ pathway. HepG2-ΔRaf-1:ER cells were transfected with 0.6 μg of reporter plasmid and 0.25 μg of SV-βGal plasmid by lipofectamine technique, as described previously (Mehta et al., 1996). Cells were washed after 12 h, and after another 12 h the cells were treated with 1 μM ICI182,780 for 36 h, and the controls were treated with ethanol. PBS-washed cells were harvested in 250 mM Tris-Cl, pH 7.5, and lysed in the lysis buffer. The luciferase activities of the cell lysates were measured according to the manufacture's recommendations (Promega). Luciferase assays were carried out in triplicate. In FIG. 6, the data are shown as means of three experiments and the fold induction represents the difference between the means of the samples with ICI182,780 and that of the control. Luciferase activity was normalized for β-galactosidase activity.

To study the role of serine/threonine protein kinases in the activation of the LDL receptor promoter by p42/44$^{MAPK}$, HepG2 cells were transiently transfected with construct A. Sixteen hours after transfection, the cells were treated for 1 h with the indicated inhibitor, and then with ICI182,780 in the continued presence of inhibitor. Although experiments were performed with a 2-day expression period, subsequent experiments revealed that similar phenomenon were observed after a shorter period of expression. Kinetic studies showed that the blocking effect of 50 μM was complete as soon as the activation of the low density lipoprotein receptor promoter was significant, i.e., after 4 to 6 h of treatment with the HDAC inhibitor.

EXAMPLE 6
DNA Synthesis Analysis

Proliferation was measured with the [$^3$H]thymidine uptake assay (Amersham), with [$^3$H]thymidine (1.0 μCi/ml) present in the medium for 4 h prior to harvesting.

EXAMPLE 7
Colony Staining

Cells were seeded at a density of 10,000 cells per 60 mm dish and maintained with or without ICI182,780 for varying periods. Colonies were stained by addition of 0.5 ml methylene blue solution for 30 min followed by washing.

EXAMPLE 8

Cell Cycle Analysis

Cells ($5 \times 10^5$) were seeded on 100 mm dishes and 2 days later the medium was replaced with medium containing 1 µM ICI182,780. After 18 h and 36 h, attached cells were trypsinized, centrifuged, washed in phosphate-buffered saline, resuspended in 1 ml phosphate-buffered saline, fixed in 1 ml of cold ethanol for overnight at 4° C., centrifuged again, washed once with saline, and resuspended in 0.1% bovine serum albumin containing 50 µg/ml ribonuclease and 50 µg/ml propidium iodide (Sigma), and then analysed in a fluoroscence-activated cell sorter (FACSORT, Becton Dickinson). Data were analysed using the Cellfit program.

EXAMPLE 9

Generation of HepG2 Cells Expressing Regulatable Form of Raf-1 Kinase

The Raf-1 serine/threonine protein kinase is a central component of the Ras/Raf/MEK/p42/44$^{MAPK}$ cascade. To examine the contribution of this cascade to the induction of LDL receptor expression, a stable HepG2 cell lines (HepG2-ΔRaf-1:ER) that express an estradiol-dependent human Raf-1 protein kinase (ΔRaf-1:ER) was generated. The eukaryotic expression vector driving the constitutive expression of the kinase domain of the oncogenic Raf-1 fused to the ligand binding domain of the estrogen receptor (ER) is shown in FIG. 1. HepG2 cells were transfected with this plasmid, and puromycin-resistant colonies were subjected to ICI182,780 treatment. ICI182,780 offers an advantage over estradiol because it has lower affinity for ER. Approximately 20 cell clones were isolated and Raf-1 kinase activity was monitored at the level of p42/44$^{MAPK}$ phosphorylation because it is expected that activation of the ΔRaf1:ER chimera in response to ICI182,780 would induce phosphorylation of MEK1/2 and p42/44$^{MAPK}$. For this purpose, selected clones were stimulated with 1 µM ICI182,780, and Western blot analysis with phospho-specific p42/44$^{MAPK}$ antibody was used to screen for dramatic induction of p42/44$^{MAPK}$ phosphorylation upon addition of ICI 182,780.

It was found that the cells were not leaky for p42/44$^{MAPK}$ phosphorylation, and most of the selected clones exhibited a dramatic increase in the phosphorylation of p42/44$^{MAPK}$ on ICI182,780 treatment (results not shown). Two clones B and S that showed maximal p42/44$^{MAPK}$ activation on ICI182,780 treatments were selected for further studies.

EXAMPLE 10

Figure 2A:
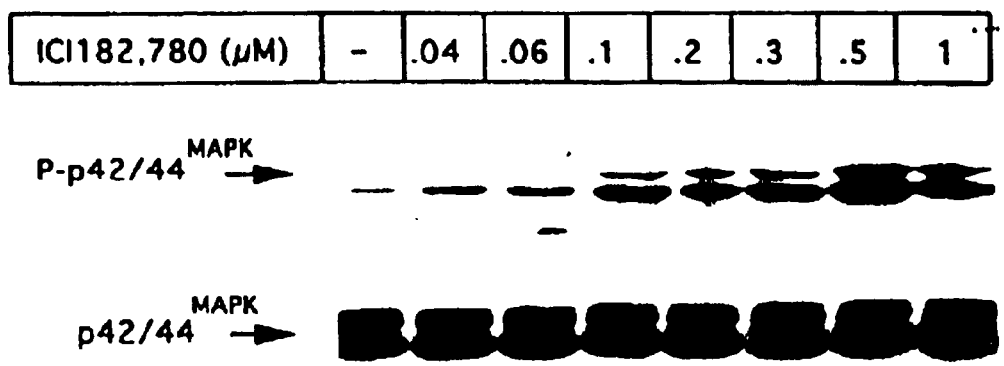
FIG. 2A shows ICI182,780 activates ΔRaf-1:ER protein that results in activation of p42/44$^{MAPK}$ phosphorylation. HepG2 cells were treated with indicated doses of ICI182,780 for 4 hours. Phospho-specific p42/44$^{MAPK}$ antibody was used to monitor p42/44$^{MAPK}$ phosphorylation/activation, and phosphorylation-independent p42/44$^{MAPK}$ antibody was used to measure total p42/44$^{MAPK}$ protein.
Figure 2B:
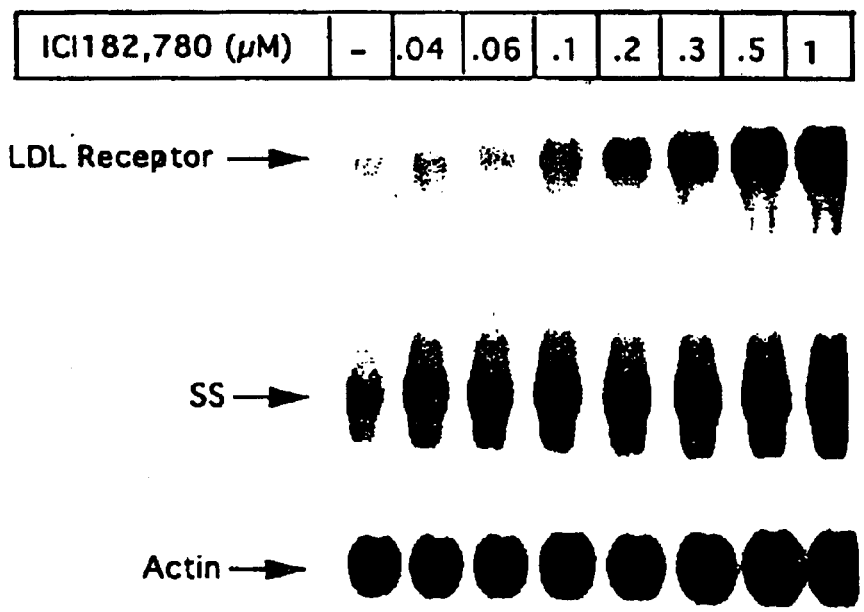
FIG. 2B shows ICI182,780 induces LDL receptor expression. Northern blotting was done under identical conditions to measure RNA levels of LDL receptor, SS, and actin genes.
Figure 2C:
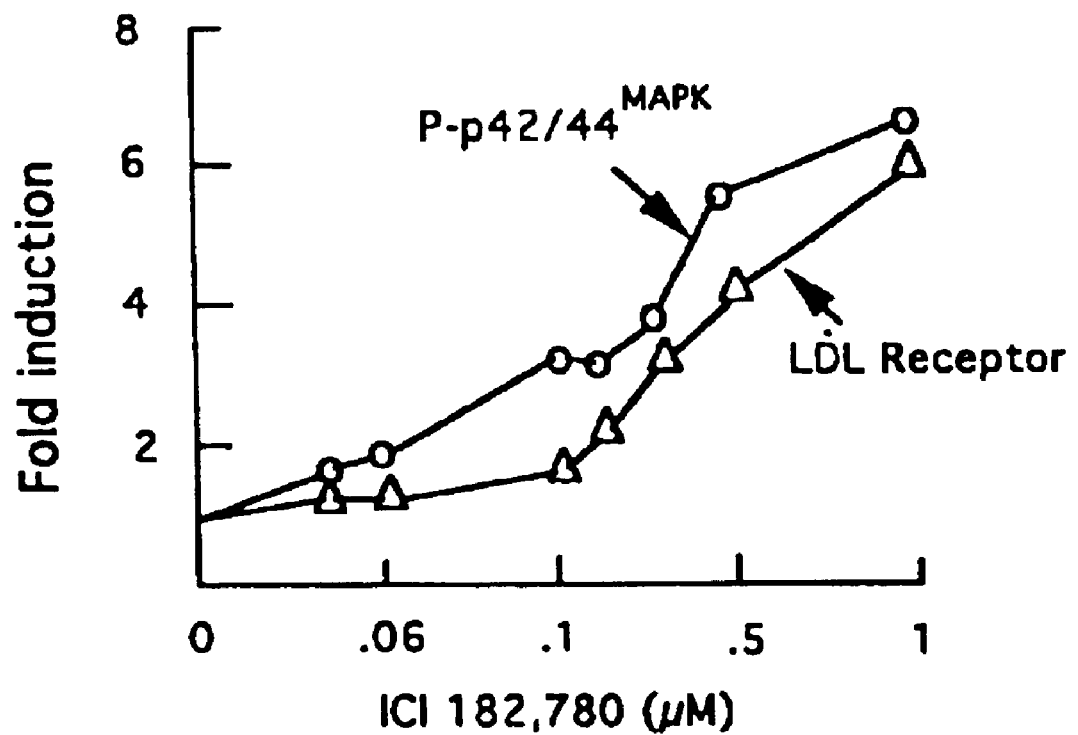
FIG. 2C shows autoradiograms quantitated by densitometry. LDL receptor mRNA levels were normalized by comparison with levels of actin. The numbers for fold induction of p42/44$^{MAPK}$ phosphorylation were derived by quantitating intensity of both bands followed by averaging. Values shown are the averages of two different experiments. Results shown are indicative of three separate experiments.

Activation of p42/44$^{MAPK}$ Cascade Is Sufficient To Induce LDL Receptor Expression In HepG2-ΔRaf-1:ER Cells To test the relationship between p42/44$^{MAPK}$ activation and LDL receptor expression, we stimulated clone B expressing ΔRaf1:ER with a range of ICI182,780 concentrations from 0 to 1 µM, because ΔRaf-1:ER activation is known to be dose-dependent in other cell lines (Woods et al. 1997). Raf-1 kinase activity was monitored at the level of p42/44$^{MAPK}$ phosphorylation and LDL receptor expression was measured under parallel conditions. As shown in FIG. 2, increases in p42/44$^{MAPK}$ phosphorylation and LDL receptor expression were dependent on ICI182,780 concentration, suggesting that the levels of p42/44$^{MAPK}$ phosphorylation determine the extent of LDL receptor expression. Similar results were obtained with clone S.

Figure 3A:
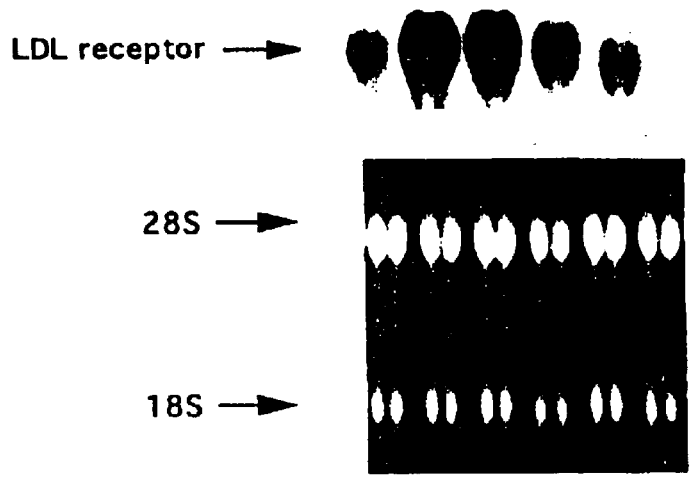
FIG. 3A shows HepG2-ΔRaf-1:ER cells pretreated for 30 min with the indicated inhibitor concentrations followed by treatment with 1 µM ICI182,780 in the presence of the inhibitor. Total RNA was analyzed by Northern blot for measuring LDL receptor mRNA levels. RNA gel was stained with ethidium bromide before blotting onto nitrocellulose paper to demonstrate equal loading of RNA in all lanes.
Figure 3B:
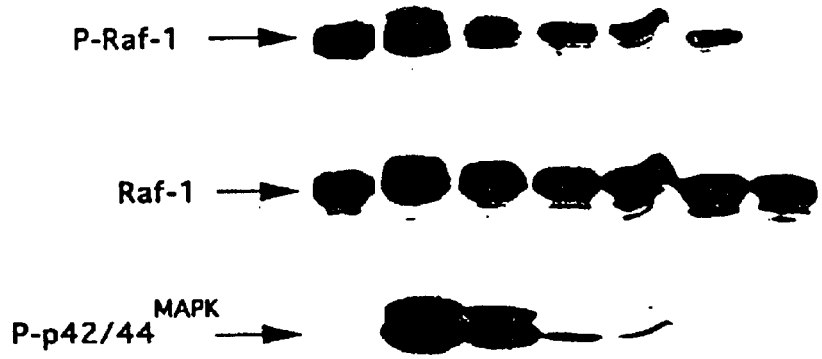
FIG. 3B shows cells were treated with the indicated concentrations of staurosporine 30 min prior to 1 µM ICI182,780 treatment. Total cell extracts were subjected to immunoblotting using the phosphorylation-independent and phospho-specific Raf-1 kinase antibodies. The same blot was later probed with the phospho-specific p42/44$^{MAPK}$ antibody.

Furthermore, staurosporine treatment resulted in loss of LDL receptor induction (FIG. 3A) due to inhibition of phosphorylation of Raf-1 kinase, and subsequently p42/44$^{MAPK}$ (FIG. 3B). This observation suggests that the increase in LDL receptor expression is due to activation of the Raf-1 kinase cascade and not due to Raf-1-independent pathway activated by ICI182,780. The mechanism by which staurosporine blocked Raf-1 kinase phosphorylation is not understood, although it seems that phosphorylation of Raf-1 at a crucial single or multiple phosphorylation sites is blocked by this agent.

To show that ΔRaf-1:ER-dependent induction of low density lipoprotein receptor expression resulted from activation of the p42/44$^{MAPK}$ cascade, HepG2-ΔRaf-1:ER cells were treated with the MEK inhibitor, PD98059. This compound selectively blocks the activation of MEK-1/2, and thereby inhibits phosphorylation and activation of p42/44$^{MAPK}$ in HepG2 cells (Kumar et al., 1998; Singh et al., 1999).

As expected, exposure of HepG2-ΔRaf-1:ER cells to 20 µM PD98059 for 30 min before ΔRaf-1:ER activation inhibited phosphorylation and activation of p42/44$^{MAPK}$ (data not shown). At the same time, PD98059 significantly inhibited p42/44$^{MAPK}$ induced LDL receptor expression (FIG. 3A), indicating that the increase in LDL receptor expression is mediated in large part via p42/44$^{MAPK}$-dependent signaling pathways.

EXAMPLE 11

Induction of LDL Receptor Expression Follows p42/44$^{MAPK}$ Activation

Figure 4A:
FIG. 4A shows HepG2-ΔRaf-1:ER cells were treated with ICI182,780 (1 µM) and total RNA was extracted at the indicated times. LDL receptor and SS mRNA levels were determined by Northern blotting. Results shown are indicative of two separate experiments.
Figure 4B:
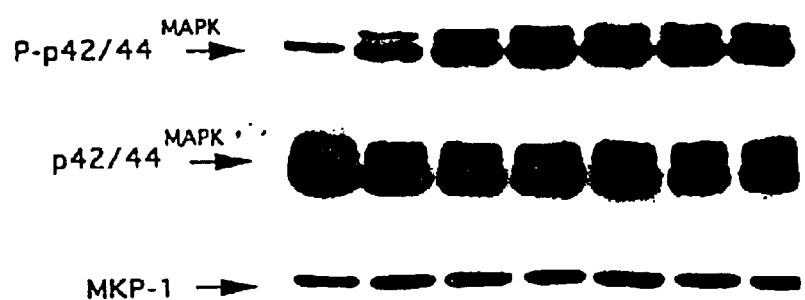
FIG. 4B shows p42/44$^{MAPK}$ phosphorylation determined under parallel conditions by immunoblotting with phosphorylation-independent and phosphorylation-specific p42/44$^{MAPK}$ antibodies.
Figure 4C:
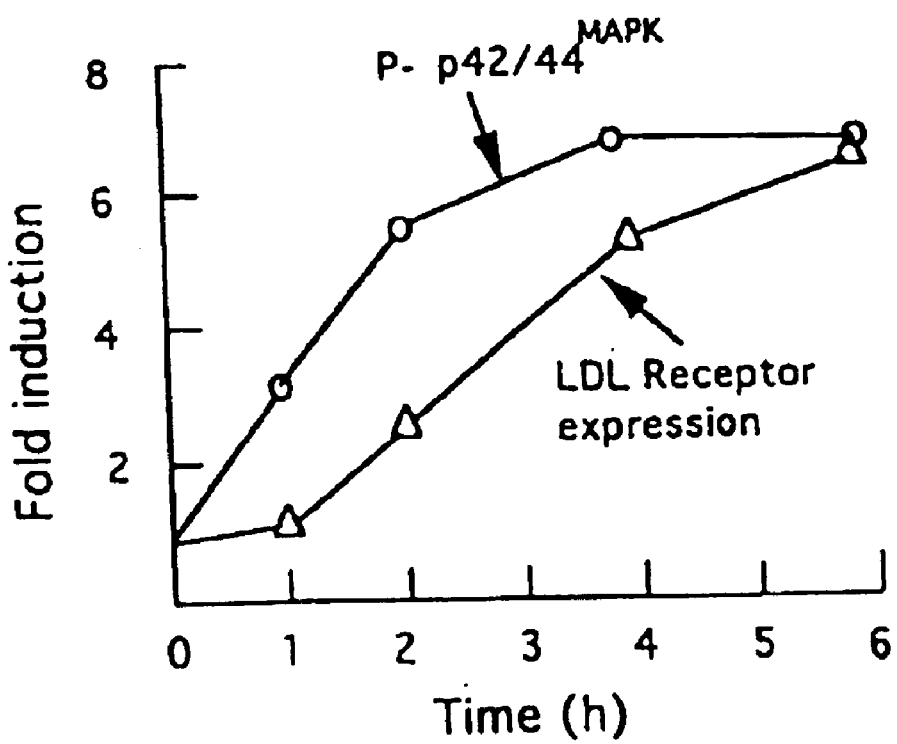
FIG. 4C shows RNA levels observed in FIG. 4A were normalized by comparison with levels of actin (not shown). The numbers for fold induction of p42/44$^{MAPK}$ phosphorylation observed in FIG. 4B were derived by quantitating intensity of both bands followed by averaging and are approximate representation. The amount of total p42/44$^{MAPK}$ proteins were identical under all the conditions tested. Values obtained from cells cultured in the absence of ICI182,780 were set at 1, and values shown are average of two different experiments.

The rapidity of Raf-1 kinase mediated-p42/44$^{MAPK}$ activation and induction of LDL receptor expression were determined. HepG2-ΔRAf-1:ER cells were stimulated with 1 µM ICI182,780 for varying periods from 1 to 16 h and the extent of p42/44$^{MAPK}$ phosphorylation and LDL receptor expression were measured. As shown in FIG. 4B, phosphorylation was clearly detected after 1 h of ICI182,780 treatment with maximal response achieved at 2 h. Prolonged treatment with ICI182,780 led to constitutive phosphorylation of the p42/44$^{MAPK}$ followed by maximal induction of LDL receptor expression within 3–4 h (FIG. 4), suggesting that LDL receptor expression responds to p42/44$^{MAPK}$ activation in a delayed manner.

EXAMPLE 12

Sterols Suppresses p42/44$^{MAPK}$-induced LDL Receptor Expression

Figure 5A:
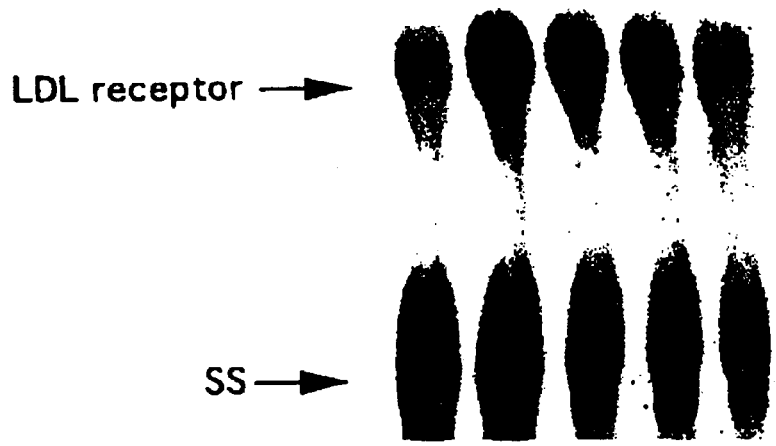
FIG. 5A shows Northern blot analysis of LDL receptor expression in the absence or presence of sterols in ICI182,780-treated HepG2-ΔRaf-1:ER cells. Cells either untreated or pretreated with different concentrations of sterols (1, 2 or 5 µg/ml 25-hydroxycholesterol and 10 µg/ml cholesterol) were induced with ICI182,780 (1 µM) for 4 h. Total RNA was subjected to Northern blotting to determine mRNA levels of LDL receptor and squalene synthase. Ethidium bromide staining of RNA gel before blotting onto a Immobilon membrane was done to demonstrate equal loading of RNA in all lanes.
Figure 5B:
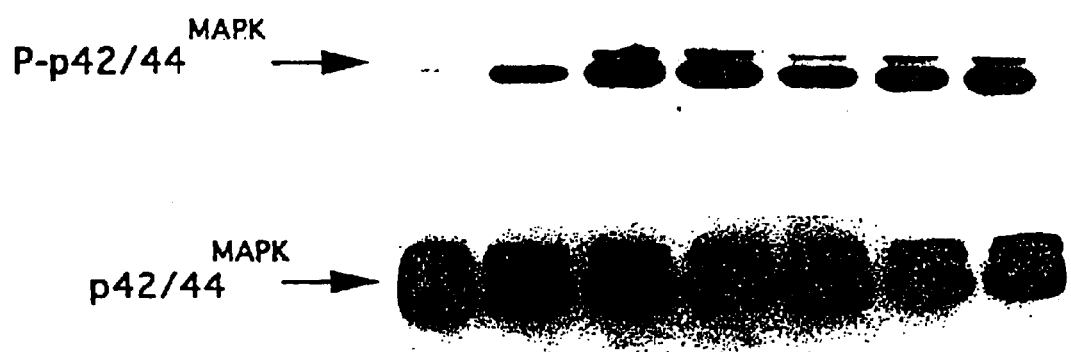
FIG. 5B shows comparison of ICI182,780-dependent p42/44$^{MAPK}$ phosphorylation in the absence or presence of sterols in HepG2-ΔRaf-1:ER cells. Cells were either untreated or pretreated with sterols (2 µg/ml 25-hydroxycholesterol and 10 µg/ml cholesterol) for 30 min followed by treatment with ICI182,780 (1 μM) for 1 hours, 2 hours, and 4 hours. Lysates were subjected to SDS-PAGE followed by immunoblotting with anti-phosphop-42/44$^{MAPK}$.

An experiment was designed to explore the ability of sterols to downregulate LDL receptor expression in the presence, as compared to the absence of ICI182,780 (FIG. 5). This experiment was repeated twice, with virtually identical results each time. In this experiment, the cells were exposed to increasing concentrations of sterols at 37° C. for 4 h, and total RNA was subjected to Northern blot analysis. In the presence of ICI182,780 (as in its absence), sterols induced a marked, concentration-dependent down-regulation of the LDL receptor expression (FIG. 5A). For each sterol concentration examined, however, LDL receptor levels in the presence of sterols were significantly lower than those seen in the absence of ICI182,780. Moreover, the effect of sterols is mediated without affecting ICI182,780-induced p42/44$^{MAPK}$ activation (FIG. 5B).

EXAMPLE 13

A LDL receptor promoter/reporter construct is activated by ICI182,780 in HepG2-ΔRaf-1:ER cells Because the primary effect of p42/44$^{MAPK}$ activation is exerted at the transcriptional levels, it was next determined whether ICI182,780 treatment modulated activity of the low density lipoprotein receptor promoter. A low density lipoprotein receptor promoter/luciferase reporter construct A (Mehta et al., 1996), containing promoter sequences from −273 to +35, was transfected into HepG2-ΔRaf-1:ER cells. Both sets of transfected cells were exposed to ICI182,780 for 36 h, after which luciferase activity was determined.

As shown in FIG. 6, luciferase expression driven by the LDL receptor promoter increased 4 to 6-fold following ICI182,780 treatment, whereas virtually no change in luciferase activity was observed in transfected cells containing the promoterless luciferase vector. Promoter activation was detected with ICI182,780 concentrations as low as 0.5 μM. Interestingly, transiently transfected construct was also activated upon addition of ICI182,780 to a similar degree than the endogenous human low density lipoprotein receptor gene. These results indicate that the effect of ICI182,780 was realized at the level of low density lipoprotein receptor transcription.

In addition to changes in gene transcription, changes in mRNA stability might also contribute to the induction or repression of mRNAs following ΔRaf-1:ER activation. Northern blot analysis of LDL receptor mRNA expression in HepG2 cells following inhibition of transcription with actinomycin D revealed that either in the presence or absence of ICI182,780, low density lipoprotein receptor mRNA levels decayed with a half-life of 2 h (data not shown) indicating that, in this case, changes in mRNA stability are unlikely to contribute to elevation of low density lipoprotein receptor mRNA levels by ΔRaf-1:ER. Thus, maintained elevation of LDL receptor mRNA expression in response to ΔRaf-1:ER activation requires continued gene transcription.

Figure 7A:
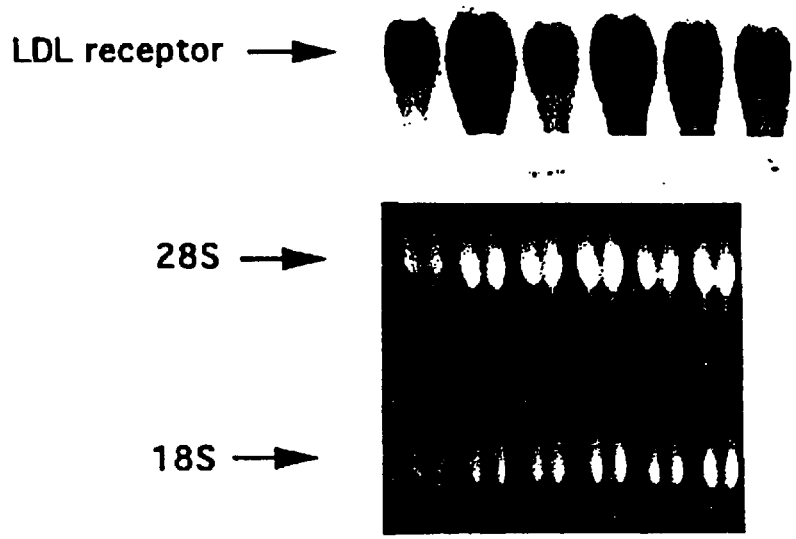
FIG. 7A shows Northern blot analysis of cells exposed to curcumin before ICI182,780 (1 μM) treatment.
Figure 7B:
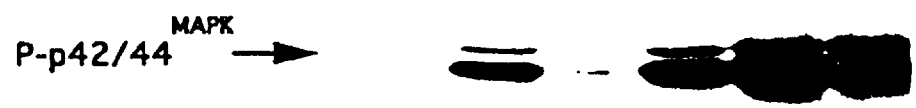
FIG. 7B shows Western blot analysis of cells grown and treated under identical conditions. Phospho-specific p42/44$^{MAPK}$ antibody was used to monitor phosphorylation levels of p42/44$^{MAPK}$, and phosphorylation-independent p42/44$^{MAPK}$ antibody was used to show equal amounts of p42/44$^{MAPK}$ protein present in each lane (data not shown).

As expected from the above studies, transcriptional effects of ICI182,780 on the human LDL receptor promoter is suppressed by staurosporine or PD98059 treatment (FIG. 6). To find an inhibitor that selectively blocks a step downstream of p42/44$^{MAPK}$, sixteen hours after transfection, the cells were treated for 1 h with a variety of protein kinase inhibitors, and then ICI182,780 was added in the continued presence of inhibitor. Curcumin (1,7-bis [4-hydroxy-3-methoxyphenyl]-1,6-heptadiene-3,5-dione) completely suppressed the activating effect of ICI182,780 in a dose-dependent manner, without affecting ICI182,780-dependent p42/44$^{MAPK}$ activation (FIG. 7).

To determine the effects of curcumin on the LDL receptor promoter in a chromatin context, HepG2-ΔRaf-1:ER cells were used. In these cells, the increase in low density lipoprotein receptor expression caused by ICI182,780 was again totally suppressed by 60 μM curcumin. Kinetic studies showed that the blocking effect of curcumin was complete as soon as the activation of the low density lipoprotein receptor expression was significant, i.e., 4 to 6 h of treatment with curcumin.

EXAMPLE 14

Activation of Raf-1/MEK/p42/44$^{MAPK}$ Inhibits DNA Synthesis And Induces Cell Growth Arrest Low levels of Raf-1 kinase activity elicit a mitogenic response whereas high levels of this kinase activity elicit cell cycle arrest (Kerkhoff and Rapp, 1998; Sewing et al., 1997). To test the effect of Raf-1 activation on cell growth, HepG2-ΔRaf-1:ER cells were treated with ICI182,780 and the effects of induced p42/44$^{MAPK}$ on cells grown in the presence of ICI182,780 (1 μM) was analysed by several parameters.

Figure 8A:
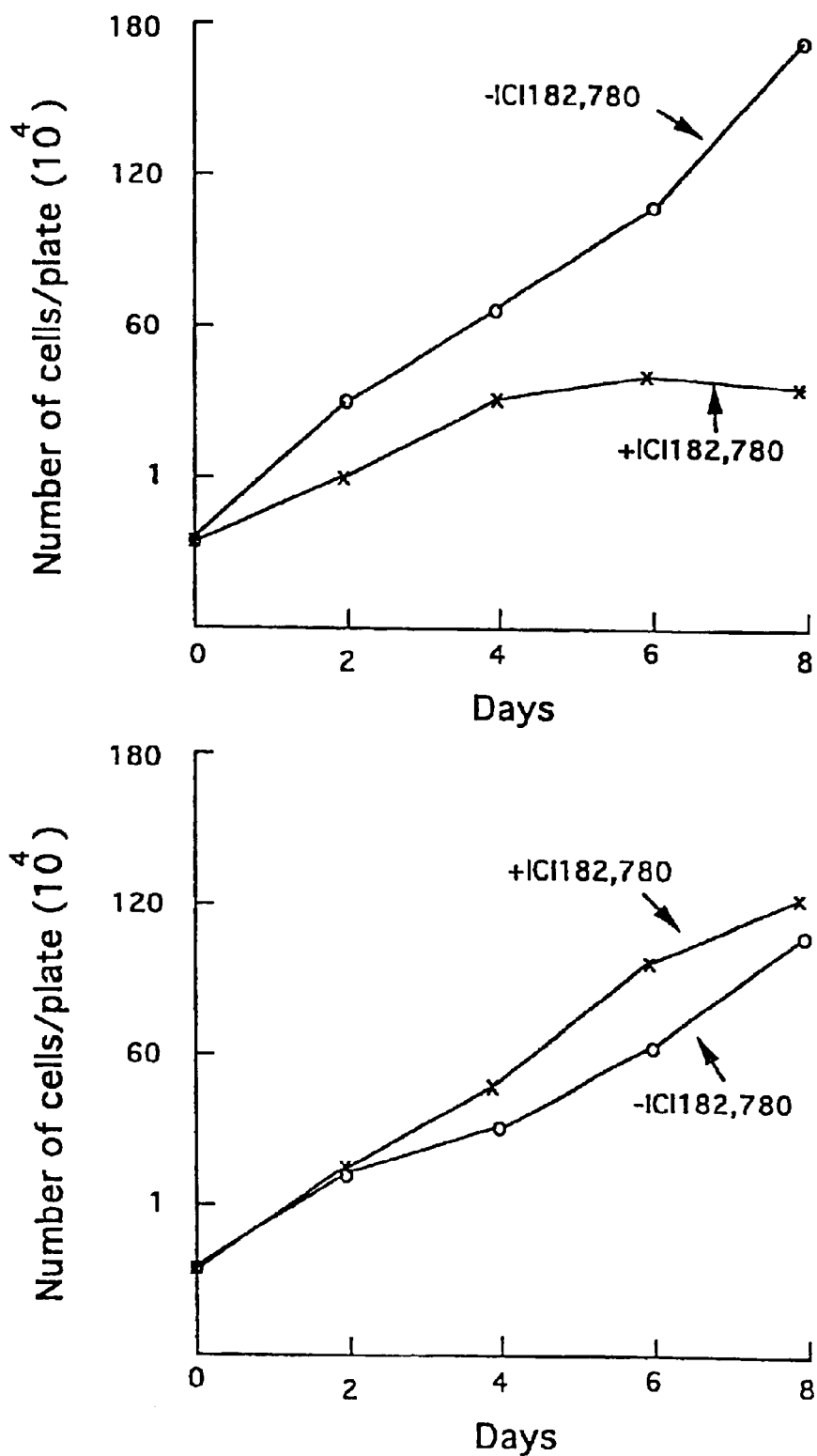
FIG. 8A shows growth curves of HepG2 cells (top panel) and HepG2-ΔRaf-1:ER cells (bottom panel) grown in the absence or presence of ICI182,780. Log-phase cells were seeded at $10^5$ cells per 60 mm dish. After 36 h the medium was changed to medium containing either 1 μM ICI182,780 or no ICI182,780. At the indicated times, cells were trypsinized and counted.
Figure 8B:
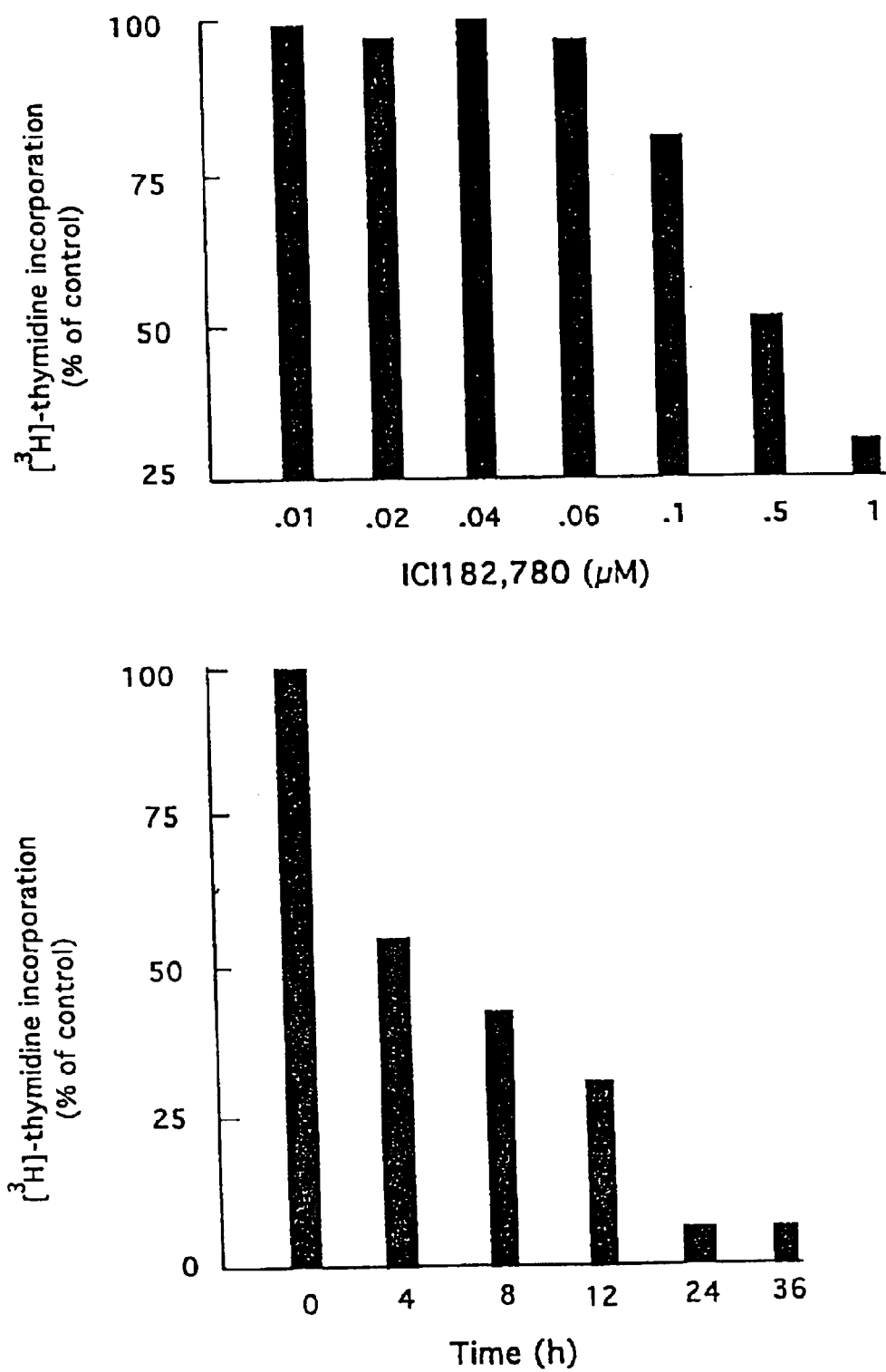
FIG. 8B shows effects of ICI182,780 treatments on [$^3$H]thymidine incorporation in HepG2-ΔRaf-1:ER cells. Cells in a 24-well dishes were either treated with different ICI182,780 concentrations from 0 to 1 μM for 18 h (top panel) or with 1 μM of ICI182,780 for time periods as indicated in the abscissa of the graph (bottom panel). DNA synthesis was measured by the incorporation of [$^3$H]thymidine during the final 4 h. Each point represents the mean of three determinations and is representative of at least two independent experiments.
Figure 9:
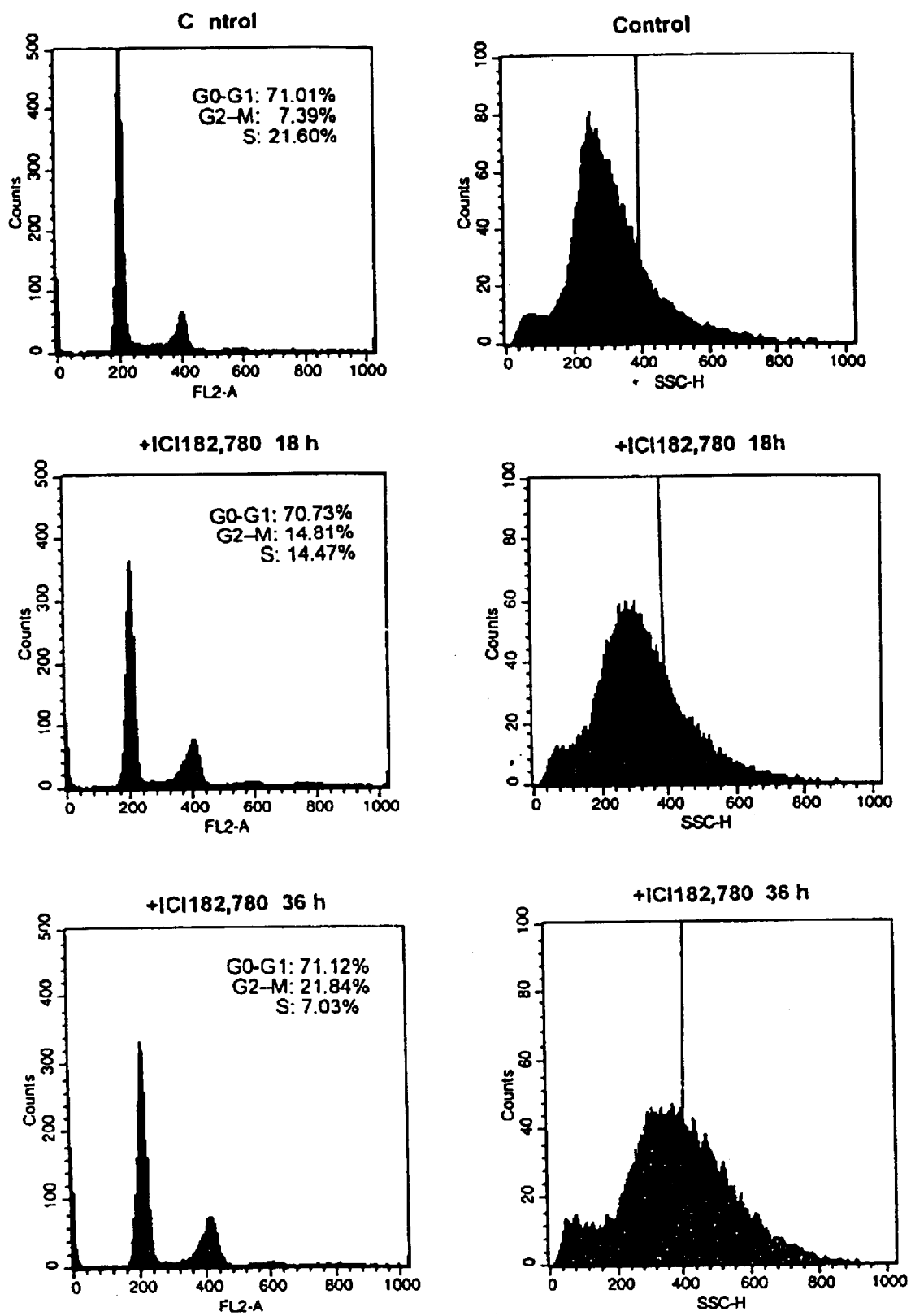
FIG. 9 shows cell cycle analysis of HepG2-ΔRaf-1:ER cells after 18 hours and 36 hours of 1 μM ICI182,780 treatment. The percentage of cells in the G1, S and G2 phases of the cell cycle is given for the control and ICI182,780 treated cells.

As shown in FIG. 8A, ICI182,780 treatment arrested the growth of HepG2-ΔRaf-1:ER cells, while no growth arrest was seen in HepG2 cells. Moreover, when the effect of p42/44$^{MAPK}$ induction on DNA synthesis was monitored, an inhibition of DNA synthesis which tightly correlated with the increase in p42/44$^{MAPK}$ activity was observed (FIG. 8B). Thus, Raf-1 kinase activation causes inhibition of DNA synthesis in HepG2 cells. Furthermore, growth arrest was associated with a modest increase in the fraction of cells found in the G2/M phase with a concomitant decrease in S phase of the cell cycle (FIG. 9). Consistent with the reduced growth, ICI182,780 treatment reduced their ability to form colonies (results not shown).

Figure 10:
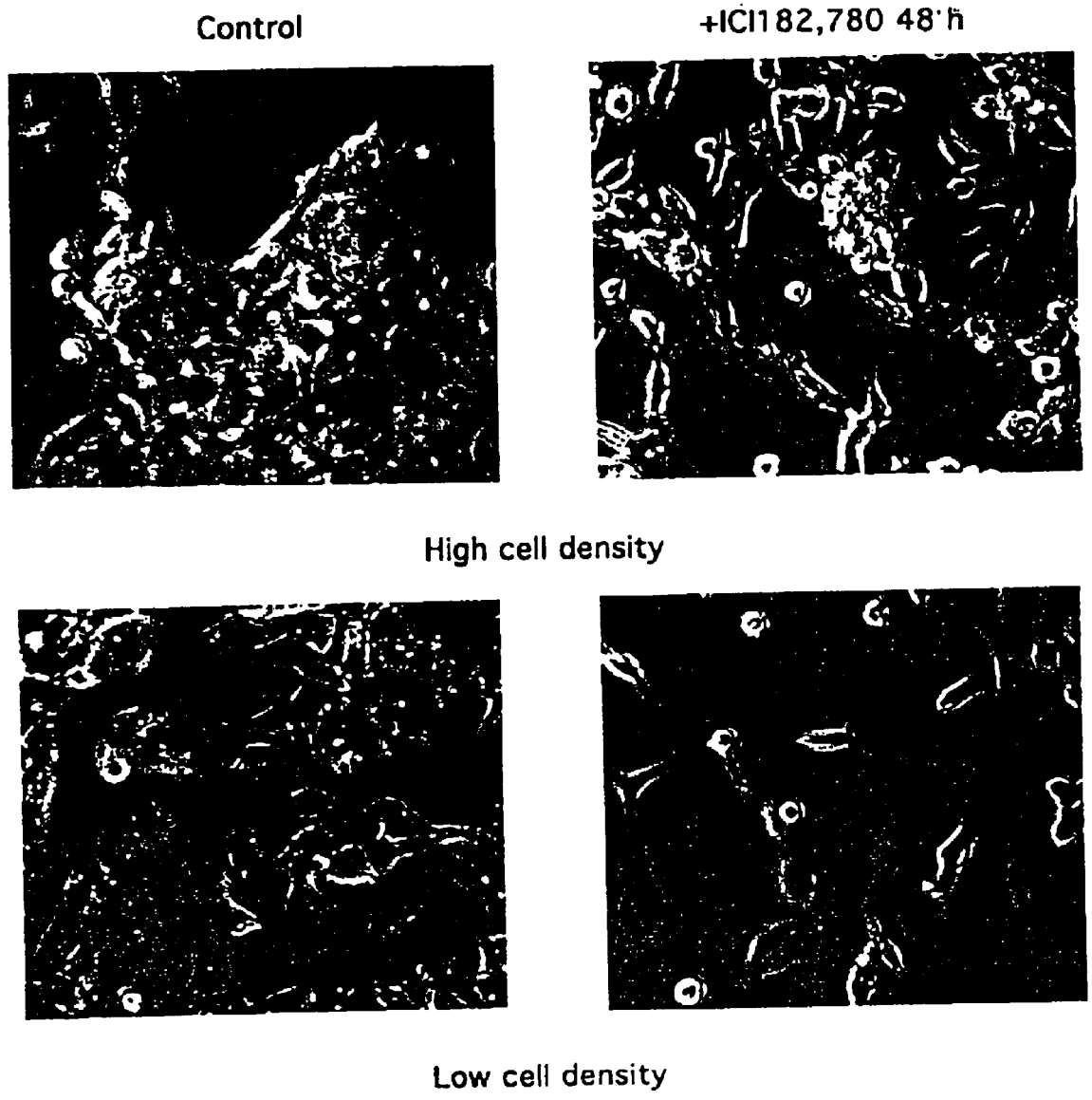
FIG. 10 shows morphological appearance of control and ICI182,780-treated HepG2-ΔRaf-1:ER cells. Cells treated with 1 μM of the ICI182,780 for 24 h were examined by optical microscopy. Cutures that were subjected to ICI182,780 treatment did not exhibit membrane blebbing and/or increase in the number of rounded and/or detached cells. Representative photomicrographs of HepG2-ΔRaf-1:ER cells either untreated or treated with ICI182,780 were taken at low and high cell density regions of the cultured plate by using microscope.

Furthermore, light microscopic examination of HepG2-ΔRaf-1:ER cells at various times after ICI182,780 treatment revealed that untreated and treated cells could easily be distinguished morphologically. FIG. 10 shows that treated cells appeared larger with neuronal like structures (i.e. filopodia), and less refractile than untreated cells. In addition, there was no indication that ICI-treated cells were under stress or dying (i.e., no extensive vacuolization, or micronuclei formation). The phenotype seen in ICI182,780-treated cells may resemble the situation of terminal differentiation, in which cells (for example, neurons) show differentiation in the absence of DNA replication.

Figure 11:
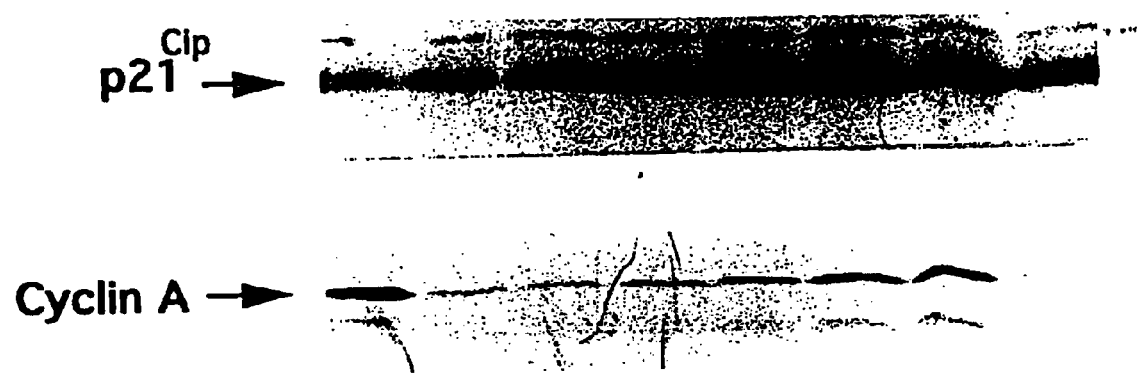
FIG. 11 shows activation of the ΔRaf-1:ER protein in HepG2-ΔRaf-1:ER cells by ICI182,780 leads to suppression of cyclin A expression and upregulation of the cyclin dependent kinase inhibitor p21$^{Cip}$. Cells were cultured in the absence or presence of 1 μM ICI182,780. Equal amounts of total protein (40 μg) were resolved by SDS-PAGE, transferred to Immobilon P membrane and probed with antibodies specific for cyclin A and p21$^{Cip}$.

The expression of cyclin A is strongly induced when the cells enter the S phase. Cyclin A protein expression is therefore an indicator for the induction of S phase and cell proliferation. Treatment of HepG2-ΔRaf-1:ER cells with ICI182,780 caused a strong down-regulation of the expression of the cyclin A protein (FIG. 11), underlining the antiproliferative character of the high-intensity Raf signals. At the same time, a strong increase in p21$^{Cip1}$ expression between 30 and 120 min of ICI182,780 treatment was detected. The high levels of p21$^{Cip1}$ were sustained for at least 24 h in HepG2-ΔRaf-1:ER cells following ICI182,780 stimulation. These results suggest that sustained expression of p21$^{Cip1}$ could be responsible for ICI182,780-induced growth inhibition in HepG2-ΔRaf-1:ER cells.

Discussion

In this study, by using a regulatable form of Raf-1 kinase, there is direct evidence that exclusive activation of the Raf-1/MEK/p42/44$^{MAPK}$ cascade induces LDL receptor expression in HepG2 cells to the same magnitude as that induced by cytokines/growth factors in these cells. The specificity of the involvement of p42/44$^{MAPK}$ was established by using a MEK inhibitor, PD98059, suggesting that although Raf-1 kinase may activate multiple signaling cascades, it is the activation of p42/44$^{MAPK}$ that is solely responsible for ICI182,780-induced LDL receptor expression in HepG2-ΔRaf-1:ER cells. The observation that the magnitude and duration of p42/44$^{MAPK}$ is a key determinant in regulating LDL receptor expression reveals the direct relationship between p42/44$^{MAPK}$ activation and extent of LDL receptor induction.

There is also evidence for the induction of LDL receptor expression by activation of p42/44$^{MAPK}$ cascade under two different sets of experimental conditions in which the chromatin structure of the DNA template differed: transient transfection of the human LDL receptor gene promoter and a natural chromatin environment for an endogenous gene. Because transfected plasmids do not show a canonical nucleosomal structure, data obtained in transient-transfection assays have been interpreted as indicating that relevant targets of p42/44$^{MAPK}$ are not histones but rather are nonhistone nuclear proteins. The fact that p42/44$^{MAPK}$ translocates to nuclei following stimulation suggests that enhancement of transcription factor activity by direct or indirect interaction with phosphorylated p42/44$^{MAPK}$ may be physiologically relevant (Treisman et al., 1996). It is therefore conceivable that the activation of the MAPK cascade modifies phosphorylation status of transcription factors or other nonhistone chromatin-associated proteins.

Recently, sterol-independent insulin- and oncostatin-induced LDL receptor expression have been related to phosphorylation of two different nuclear factors via p42/44$^{MAPK}$. Kotzka et al. have suggested that modification of SREBP is responsible for insulin-induced LDL receptor expression (Kotzka et al., 2000), whereas, Lui et al. (2000) have shown data supporting the conclusion that phosphorylation of a nuclear factor interacting within the TATA box region induces LDL receptor transcription. However, due to sterol-sensitive nature of the p42/44$^{MAPK}$-induced LDL receptor expression as indicated in the present studies, it is difficult to understand how activation of the p42/44$^{MAPK}$ cascade alone by insulin or oncostatin can confer sterol-resistant induction to the low density lipoprotein receptor expression. Also, the reasons for two different nuclear targets of p42/44$^{MAPK}$ are not clear at present. However, participation of an additional signaling pathway(s) in concert with p42/44$^{MAPK}$ may account for induction of low density lipoprotein receptor transcription by the above agents. The availability of the HepG2-ΔRaf-1:ER cell lines will greatly help us in defining the specific target(s) of the p42/44$^{MAPK}$ cascade whose modification induces low density lipoprotein receptor transcription.

The induction of LDL receptor expression by mitogens, growth factors, and cytokines provides a critical link between cell growth and membrane biosynthesis. A positive relationship between the rate of cell growth and the LDL receptor expression has been reported by other investigators (reviewed by Brown and Goldstein, 1990), suggesting that these two phenomena are clearly related. A simple interpretation of the results reported is that the increase in LDL receptor expression stimulated by cell growth is meant to provide proliferating cells with additional cholesterol for the synthesis of new membranes.

In order to understand the molecular mechanisms governing this phenomenon, information concerning the relationships that exist between the effects of p42/44$^{MAPK}$ activation on DNA synthesis and on LDL receptor expression was sought. By using several criteria, it was shown that the activation of p42/44$^{MAPK}$ induces LDL receptor promoter activity and concomitantly causes a decrease in cell proliferation and upregulation of genes associated with growth arrest. Together these results support the notion that neither DNA synthesis nor cellular proliferation appears to be a prerequisite for p42/44$^{MAPK}$-induced LDL receptor expression. Thus, despite their apparent relationship, the processes of DNA synthesis and modulation of LDL receptor expression can occur quite independently of each other through p42/44$^{MAPK}$ cascade. The growth-independent regulation of LDL receptor expression by activated p42/44$^{MAPK}$ cascade will also explain cytokine and growth factor-induced LDL receptor transcription without affecting cellular proliferation or DNA synthesis (Pak et al., 1996; Shiota et al., 1992).

Recent reports have provided evidence that a non-sterol product of mevalonate metabolism (reviewed by Goldstein and Brown, 1990), perhaps an isoprenoid product like farnesylpyrophosphate play an essential role in the regulation of DNA synthesis and cell growth. One well known effect of LDL internalization and degradation via the LDL receptor pathway is down-regulation (suppression) of sterol-sensitive enzymes including SS, HMG-CoA reductase, and HMG-CoA synthase. Accordingly, it is possible that the p42/44$^{MAPK}$-induced constitutive expression of LDL receptor expression dramatically decreases concentrations of these mevalonate products required for DNA synthesis. Experiments were conducted to explore the effects of supplementing cultured cells with mevalonate or intermediates. Addition of these intermediates had no significant effect on p42/44$^{MAPK}$-induced inhibition of DNA synthesis (results not shown), suggesting that the decrease in DNA synthesis is not due to reduction in the amounts of mevalonate pathway intermediates. Remarkably, the ability of Raf-1 kinase to elicit cell cycle arrest has been strongly associated with its ability to induce the expression of the cyclin-dependent kinase inhibitor p21$^{Cip1}$ in NIH3T3-ΔRaf-1:ER cells (Sewing et al., 1997). It is thus conceivable that the growth arrest in HepG2 cells is largely, if not completely, due to the induction of p21$^{Cip1}$ expression. Consistent with the role of p21$^{Cip1}$ in growth arrest in HepG2 cells (Niculescu et al., 1998), it was found that the expression of this gene was increased in a p42/44$^{MAPK}$-dependent manner. It is possible that the constitutive activation of Raf-1/MEK/p42/44$^{MAPK}$ cascade silences the components of the cell cycle machinery by the overexpression of the p21$^{Cip1}$, and as a result, the DNA synthesis as well as cell division is inhibited, leading to accumulation of cells corresponding to cell cycle arrest in the G1 and G2-M phases. Such Raf-1-mediated growth arrest may be an important mechanism to prevent cells from progressing to a state of unlimited proliferation, thereby serving as an alternative to apoptosis.

Finally, it is surprising to note that curcumin, the yellow pigment in turmeric (Curcuma longa) and curry, a widely used Indian herbal medicine, blocked p42/44$^{MAPK}$-dependent LDL receptor induction (Mukhopadhyay et al., 1982). Curcumin and its analogues have been reported to possess antioxidant, anti-inflammatory, and hypolipidemic activities. Recently, it has been reported that curcumin caused dramatic reductions in total cholesterol and lipoprotein abnormalities developed under diabetic conditions and/or associated with high cholesterol diet intake in rats (Babu et al., 1997). Furthermore, curcumin extracts have also been shown to be effective against increases in plasma cholesterol in rabbits with experimental atherosclerosis (Ramirez-Tortosa et al., 1999). In fact, curcumin's influence on various lipoprotein-associated cholesterol fractions resembles drugs used for lowering plasma cholesterol concentrations (cholestyramine, mevinolin, lovastatin and simvastatin). Hypocholesterolemic drugs decrease LDL-cholesterol presumably by stimulating receptor mediated removal of LDL. However, the inhibition of LDL receptor expression in hepatic cells by curcumin suggests an altogether different mechanism of action possibly involving inhibition of lipoproteins biosynthesis.

Thus, it is concluded that specific activation of the Raf-1/MEK/p42/44$^{MAPK}$ kinase cascade in HepG2 cells, independent of other "upstream" factors, leads to induction of LDL receptor transcription. This is the first report demonstrating the importance of a p42/44$^{MAPK}$ signaling pathway in growth-independent regulation of LDL receptor expression and showing that LDL receptor expression and cell growth can be regulated independently. Availability of the HepG2-ΔRaf-1:ER cells provide the groundwork for future studies examining the molecular mechanisms regulating LDL receptor expression by specifically activating p42/44$^{MAPK}$ signaling cascade. The present findings further underscore the important and central role of the MAPK pathway in regulating LDL receptor expression and may be of considerable potential significance for the development of new signal transduction-based approaches for the treatment of hypercholesterolemia.

The following references were cited herein:

Babu and Srinivasan, Mol Cell Biochem 166:169–175.
Bornfeldt et al., J. Clin. Investig. 100:875–885 (1997).
Brown and Goldstein, Science 232:34–47 (1986).
Casey et al., Proc. Natl. Acad. Sci. USA 86:8323–8327 (1989).
Dhawan et al., J Lipid Res 40:1911–1919 (1999).
Fairbank et al., J. Biol. Chem. 259:1546–1551 (1984).
Garrington and Johnson, Current Opinion in Cell Biol. 11: 211–218 (1999).
Goldstein and Brown, Nature 343: 425–430 (1990).
Gutierrez et al., EMBO J 8:1093–1098 (1989).
Habenicht et al., J. Biol. Chem. 255:5134–5140 (1980).
Hancock et al., Cell 57:1167–1177 (1989).
Kerkhoff and Rapp, Cancer Res 58:1636–1640 (1998).
Kotzka et al., J Lipid Res 41: 99–108 (2000).
Kumar et al., J. Lipid Res. 38, 4220–4228 (1997).
Kumar et al., J Biol Chem 273: 15742–15748 (1998).
Liu et al., J Biol Chem 275:5214–5221 (2000).
Marshall, Cell 80:179–185 (1995).
Mehta et al., J Biol Chem 271:33616–33622 (1996).
Mehta and Miller, Trends in Cardiovas Med 9:201–205 (1999).
Mukhopadhyay et al., Agents & Actions 12:508–515 (1982).
Niculescu et al., Mol Cell Biol 18: 629–643 (1998).
Pak et al., J. Lipid. Res. 37: 985–998 (1996).
Pang et al., J Biol Chem 270, 13585–13588 (1995).
Pumiglia and Decker, Proc. Natl. Acad. Sci. USA 94: 448–452 (1997).
Ramirez et al., Atherosclerosis 147:371–378 (1999).
Robinson and Cobb, Curr Opin Cell Biol 9:180–186 (1997).
Schaeffer and Weber, Mol Cell Biol 19:2435–2444 (1999).
Sewing et al., Mol Cell Biol 17:5588–5597 (1997).
Shiota et al., Proc Natl Acad Sci USA 89: 373–377 (1992).
Singh et al., J. Biol. Chem. 274: 19593–19600 (1999).
Treisman, Curr. Opin. Cell. Biol. 8:205–215 (1996).
Whitmarsh and Davis, J Mol Med 74: 589–607 (1996).
Woods et al., Mol Cell Biol 17: 5598–5611 (1997).

Any patents or publications mentioned in this specification are indicative of the levels of those skilled in the art to which the invention pertains. Further, these patents and publications are incorporated by reference herein to the same extent as if each individual publication was specifically and individually indicated to be incorporated by reference.

One skilled in the art will appreciate readily that the present invention is well adapted to carry out the objects and obtain the ends and advantages mentioned, as well as those objects, ends and advantages inherent herein. The present examples, along with the methods, procedures, treatments, molecules, and specific compounds described herein are presently representative of preferred embodiments, are exemplary, and are not intended as limitations on the scope of the invention. Changes therein and other uses will occur to those skilled in the art which are encompassed within the spirit of the invention as defined by the scope of the claims.

What is claimed is:

1. A method of inducing low density lipoprotein receptor expression through the sole activation of extracellular-signal regulated kinase (p42/44$^{MAPK}$), comprising the step of:

contacting an HepG2-ΔRaf-1:ER cell line with a compound that activates the extracellular-signal regulated kinase, p42/44$^{MAPK}$, wherein the activation of said kinase results in the induction of low density lipoprotein receptor expression, and wherein said compound induces a growth arrest in said cell.

2. The method of claim 1, wherein said induction of low density lipoprotein receptor expression is independent of cell growth regulation.

3. The method of claim 1, wherein the extent of said induction of low density lipoprotein receptor expression is dependent on the extent of activation of p42/44$^{MAPK}$.

* * * * *